US012806353B2

(12) United States Patent
Liu et al.

(10) Patent No.: US 12,806,353 B2
(45) Date of Patent: Nov. 24, 2026

(54) METHOD FOR EVALUATING VOLUME RESPONSIVENESS AND MEDICAL DEVICE

(71) Applicants: ZHONGDA HOSPITAL SOUTHEAST UNIVERSITY, Nanjing (CN); SHENZHEN MINDRAY BIO-MEDICAL ELECTRONICS CO., LTD., Shenzhen (CN)

(72) Inventors: Ling Liu, Nanjing (CN); Jinglei Liu, Shenzhen (CN); Jianfeng Xie, Nanjing (CN); Xiaoyong Zhou, Shenzhen (CN); Jingyuan Xu, Nanjing (CN); Jun Chen, Shenzhen (CN); Yi Yang, Nanjing (CN); Xinru Zou, Nanjing (CN); Haibo Qiu, Nanjing (CN)

(73) Assignees: SHENZHEN MINDRAY BIO-MEDICAL ELECTRONICS CO., LTD., Shenzhen (CN); ZHONGDA HOSPITAL SOUTHEAST UNIVERSITY, Nanjing (CN)

( * ) Notice: Subject to any disclaimer, the term of this patent is extended or adjusted under 35 U.S.C. 154(b) by 1275 days.

(21) Appl. No.: 17/708,037

(22) Filed: Mar. 30, 2022

(65) Prior Publication Data

US 2022/0218928 A1 Jul. 14, 2022

Related U.S. Application Data

(63) Continuation of application No. PCT/CN2019/109654, filed on Sep. 30, 2019.

(51) Int. Cl.

*A61M 16/00* (2006.01)
*A61B 5/02* (2006.01)

(Continued)

(52) U.S. Cl.

CPC .......... *A61M 16/024* (2017.08); *G16H 20/40* (2018.01); *A61M 2230/06* (2013.01); *A61M 2230/46* (2013.01)

(58) Field of Classification Search

CPC .... A61M 16/022–026; A61M 2230/06; A61M 2230/46; A61M 2016/0027;

(Continued)

(56) References Cited

U.S. PATENT DOCUMENTS

2004/0249297 A1 12/2004 Pfeiffer et al.
2011/0270097 A1 * 11/2011 Aboy .................. A61B 5/4836 600/484

(Continued)

FOREIGN PATENT DOCUMENTS

CN 101919690 A 12/2010
CN 106793959 A 5/2017
CN 108937881 A * 12/2018 ............ A61B 5/026

OTHER PUBLICATIONS

Myatra et al. The Changes in Pulse Pressure Variation or Stroke Volume Variation After a "Tidal Volume Challenge" Reliably Predict Fluid Responsiveness During Low Tidal Volume Ventilation. Crit Care Med. Mar. 2017;45(3):415-421. doi: 10.1097/CCM.0000000000002183. PMID: 27922879. (Year: 2017).*

(Continued)

*Primary Examiner* — Valerie L Woodward
*Assistant Examiner* — Mautin I Ashimiu
(74) *Attorney, Agent, or Firm* — Morgan, Lewis & Bockius LLP

(57) ABSTRACT

This disclosure provides a method for evaluating volume responsiveness and a medical device. The medical device includes a respiratory assistance device for providing respiratory support for a patient, and a first sensor for collecting physiological parameters of the patient and a processor.

(Continued)

When volume responsiveness evaluation is needed, the processor controls ventilation parameters to switch to a second ventilation parameter that may increase the variation of the intrathoracic pressure of the patient, and then uses a parameter variation capable of reflecting the heartbeat of the patient to evaluate whether the patient is volume responsive.

8 Claims, 7 Drawing Sheets

(51) Int. Cl.

| | |
|---|---|
| ***A61M 16/08*** | (2006.01) |
| ***A61M 16/10*** | (2006.01) |
| ***A61M 16/12*** | (2006.01) |
| ***A61M 16/16*** | (2006.01) |
| ***A61M 16/20*** | (2006.01) |
| ***G16H 20/40*** | (2018.01) |
| ***G16H 50/30*** | (2018.01) |

(58) Field of Classification Search

CPC .... A61M 2016/0039; A61M 2205/505; A61M 16/202; A61M 16/0808; A61M 16/1055; A61M 16/107; A61M 16/16; A61M 2016/0042; A61M 2202/0208; A61M 2205/18; A61M 2230/10; A61M 2230/205; A61M 16/125; A61M 2205/3331; A61M 2230/04; A61M 2230/30; A61M 2230/50; A61B 5/02–0295

See application file for complete search history.

(56) References Cited

U.S. PATENT DOCUMENTS

| | | | | |
|---|---|---|---|---|
| 2014/0073889 | A1* | 3/2014 | Su | A61B 5/0205 600/324 |
| 2021/0228095 | A1* | 7/2021 | Pfeiffer | A61B 5/0816 |

OTHER PUBLICATIONS

Machine_Translation_of_Description_CN108937881A (Year: 2018).*

First Office Action issued in related Chinese Application No. 201980074539.2, mailed Nov. 22, 2021, 23 pages.

Myatra, Sheila Nainan et al, "The Changes in Pulse Pressure Variation or Stroke Volume Variation After a "Tidal Volume Challenge" Reliably Predict Fluid Responsiveness During Low Tidal Volume Ventilation", Critical Care Medicine, vol. 45, Mar. 31, 2017, p. 415-421.

International Search Report issued in corresponding International Application No. PCT/CN2019/109654, mailed Jun. 23, 2020, 4 pages.

Zhou, Mei, "Research Progress in Volume Status, Fluid Responsiveness Assessment Indicators and Technologies", Shandong Medical Journal, vol. 59, No. 25, Sep. 5, 2019.

Georges, Delphine et al, "End-expiratory occlusion maneuver to predict fluid responsiveness in the intensive care unit: an echocardiographic study", Critical Care, vol. 22, Feb. 8, 2018, p. 2-7.

Guo, Fang et al., "Research Progress in Fluid Responsiveness Dynamic Assessment During Perioperative Period", Chinese Journal of Minimally Invasive Surgery, vol. 17, No. 8, Aug. 31, 2017.

* cited by examiner

METHOD FOR EVALUATING VOLUME RESPONSIVENESS AND MEDICAL DEVICE

CROSS REFERENCE TO RELATED APPLICATIONS

This disclosure is a continuation of Patent Cooperation Treaty Application No. PCT/CN2019/109654, filed on Sep. 30, 2019, which is hereby incorporated by reference.

TECHNICAL FIELD

The disclosure relates to a medical device, and in particular, to a method for evaluating volume responsiveness.

BACKGROUND

In life monitoring of a patient, hemodynamic parameters (such as blood specific viscosity, erythrocyte electrophoresis, erythrocyte sedimentation rate, and fibrinolytic system functions) may need to be monitored based on the patient's condition. When the hemodynamic parameters are unstable, the first treatment option that needs to be considered is volume resuscitation, which increases a cardiac output by increasing a volume load, so as to stabilize the hemodynamic parameters of the patient. Volume load, also referred to as cardiac preload, refers to a load before the heart muscle contracts, that is, a volume load or pressure on the ventricle during end diastole. Clinically, volume responsiveness is usually used to determine whether the increase in the volume load may lead to a corresponding increase in the cardiac output.

In an intensive care unit (ICU), the cardiac output may be increased for only half of patients with hemodynamic instability by means of the volume resuscitation. For the patients who do not have the volume responsiveness, increasing the volume load will not increase the cardiac output, but only aggravate tissue edema and hypoxia. Therefore, bedside evaluation of volume responsiveness is essential to guide clinical treatment.

A pulse pressure (referring to a difference between a systolic pressure and a diastolic pressure) may reflect the stroke volume of the heart, and therefore the pulse pressure variation (PPV) during mechanical ventilation is clinically commonly used as an evaluation indicator of the volume responsiveness. However, it is clinically found that use of a relatively small PPV value to evaluate the volume responsiveness will reduce the accuracy of the evaluation.

SUMMARY

According to a first aspect, a method for evaluating volume responsiveness is provided in an embodiment, where the method includes:

- collecting first sequence values of a parameter capable of reflecting a heartbeat of a patient within a predetermined time when a first ventilation parameter is used to control a respiratory assistance device to provide respiratory support for the patient;
- calculating a variation of the first sequence values;
- evaluating whether the patient is volume responsive based on the variation of the first sequence values, and carrying out the following steps when the variation of the first sequence values is less than or equal to a preset first threshold;
- switching the first ventilation parameter to a second ventilation parameter;

- collecting second sequence values of the parameter capable of reflecting the heartbeat of the patient within the predetermined time when the second ventilation parameter is used to control the respiratory assistance device to provide respiratory support for the patient, the second ventilation parameter being capable of increasing a variation of an intrapleural pressure of the patient compared to the first ventilation parameter;
- calculating the variation of the second sequence values; and
- evaluating whether the patient is volume responsive based on the variation of the second sequence values.

According to a second aspect, a method for evaluating volume responsiveness is provided in an embodiment, where the method includes:

- when the volume responsiveness needs to be evaluated, switching a first ventilation parameter currently used for controlling a respiratory assistance device to provide respiratory support for a patient to a second ventilation parameter, the second ventilation parameter being capable of increasing a variation of an intrapleural pressure of the patient compared to the first ventilation parameter;
- collecting second sequence values of a parameter capable of reflecting the heartbeat of the patient within a predetermined time when a second ventilation parameter is used to control the respiratory assistance device to provide respiratory support for the patient;
- calculating a variation of the second sequence values; and
- evaluating whether the patient is volume responsive based on the variation of the second sequence values.

According to a third aspect, a method for evaluating volume responsiveness is provided in an embodiment, the method including:

- detecting a compliance of a patient when the volume responsiveness needs to be evaluated;
- when the detected compliance is less than a fifth threshold, switching a first ventilation parameter currently used for controlling a respiratory assistance device to provide respiratory support for the patient to a second ventilation parameter, the second ventilation parameter being capable of increasing a variation of an intrapleural pressure of the patient compared to the first ventilation parameter;
- collecting second sequence values of a parameter capable of reflecting the heartbeat of the patient within a predetermined time when a second ventilation parameter is used to control the respiratory assistance device to provide respiratory support for the patient;
- calculating a variation of the second sequence values; and
- evaluating whether the patient is volume responsive based on the variation of the second sequence values.

According to a fourth aspect, a medical device is provided in an embodiment, where the medical device includes:

- a respiratory assistance device configured to provide respiratory support for a patient, the respiratory assistance device including a breathing circuit and a ventilation control assembly, where the breathing circuit is configured to provide a flow channel for a gas from a gas source to the patient or from the patient to an exhaust port, and the ventilation control assembly is configured to control a flow and/or a pressure of the gas in the breathing circuit;
- a first sensor configured to collect a physiological parameter of the patient, where the physiological parameter is at least used to obtain a parameter capable of reflecting a heartbeat of the patient; and a processor configured to control the ventilation control assembly by using a first ventilation parameter, receive the physiological parameter output from the first sensor, obtain, from the physiological parameter, first sequence values of the parameter capable of reflecting a heartbeat of the patient when the first ventilation parameter is used to control the respiratory assistance device to provide respiratory support for the patient, calculate the variation of the first sequence values, evaluate whether the patient is volume responsive based on the variation of the first sequence values, switch to using a second ventilation parameter to control the ventilation control assembly when the variation of the first sequence values is less than or equal to a first threshold, receive the physiological parameter output from the first sensor, obtain, from the physiological parameter, second sequence values of the parameter capable of reflecting the heartbeat of the patient when the second ventilation parameter is used to control the respiratory assistance device to provide respiratory support for the patient, the second ventilation parameter being capable of increasing a variation of an intrapleural pressure of the patient compared to the first ventilation parameter, calculate a variation of the second sequence values, and evaluate whether the patient is volume responsive based on the variation of the second sequence values.

According to a fifth aspect, a medical device is provided in an embodiment, where the medical device includes:

a respiratory assistance device configured to provide respiratory support for a patient, the respiratory assistance device including a breathing circuit and a ventilation control assembly, where the breathing circuit is configured to provide a flow channel for a gas from a gas source to the patient or from the patient to an exhaust port, and the ventilation control assembly is configured to control a flow and/or a pressure of the gas in the breathing circuit;

a first sensor configured to collect a physiological parameter of the patient, where the physiological parameter is at least used to obtain a parameter capable of reflecting the heartbeat of the patient; and a processor configured to, when volume responsiveness needs to be evaluated, switch a ventilation parameter for controlling the respiratory assistance device to provide respiratory support for the patient from a current first ventilation parameter to a second ventilation parameter, the second ventilation parameter being capable of increasing a variation of an intrapleural pressure of the patient compared to the first ventilation parameter, control the ventilation control assembly to adjust a flow and/or a pressure of the gas in the breathing circuit, receive the physiological parameter output from the first sensor when the second ventilation parameter is used to control the respiratory assistance device to provide respiratory support for the patient, obtain, from the physiological parameter, second sequence values of the parameter capable of reflecting the heartbeat of the patient, calculate a variation of the second sequence values, and evaluate whether the patient is volume responsive based on the variation of the second sequence values.

According to a sixth aspect, a medical device is provided in an embodiment, where the medical device includes:

a respiratory assistance device configured to provide respiratory support for a patient, the respiratory assistance device including a breathing circuit and a ventilation control assembly, where the breathing circuit is configured to provide a flow channel for a gas from a gas source to the patient or from the patient to an exhaust port, and the ventilation control assembly is configured to control a flow and/or a pressure of the gas in the breathing circuit;

a first sensor configured to collect a physiological parameter of the patient, where the physiological parameter is at least used to obtain a parameter capable of reflecting a heartbeat of the patient; and a processor configured to, when volume responsiveness needs to be evaluated, detect a compliance of the patient, switch a first ventilation parameter currently used for controlling the respiratory assistance device to provide respiratory support for the patient to a second ventilation parameter when the detected compliance is less than a fifth threshold, the second ventilation parameter being capable of increasing a variation of an intrapleural pressure of the patient compared to the first ventilation parameter, collect second sequence values of the parameter capable of reflecting the heartbeat of the patient within the predetermined time when the second ventilation parameter is used to control the respiratory assistance device to provide respiratory support for the patient, and evaluate whether the patient is volume responsive based on a variation of the second sequence values.

According to a seventh aspect, a method for evaluating volume responsiveness is provided in an embodiment, the method including:

collecting first sequence values of a parameter capable of reflecting a heartbeat of a patient within a predetermined time when a first ventilation parameter is used to control a respiratory assistance device to provide respiratory support for the patient;

calculating a variation of the first sequence values;

evaluating whether the patient is volume responsive based on the variation of the first sequence values, and carrying out the following steps when the variation of the first sequence values is less than or equal to a first threshold;

applying an end-expiratory occlusion to the patient to respectively obtain values of the parameter capable of reflecting the heartbeat of the patient before and after the end-expiratory occlusion; and determining whether the patient is volume responsive based on the a variation of the values of the parameter capable of reflecting the heartbeat of the patient before and after the end-expiratory occlusion.

According to an eighth aspect, a medical device is provided in an embodiment, where the medical device includes:

a respiratory assistance device configured to provide respiratory support for a patient, the respiratory assistance device including a breathing circuit and a ventilation control assembly, where the breathing circuit is configured to provide a flow channel for a gas from a gas source to the patient or from the patient to an exhaust port, and the ventilation control assembly is configured to control a flow and/or a pressure of the gas in the breathing circuit;

a first sensor configured to collect a physiological parameter of the patient, where the physiological parameter is at least used to obtain a parameter used to reflect a stroke volume of the patient and capable of reflecting a heartbeat of the patient; and a processor configured to control the ventilation control assembly by using a first ventilation parameter, receive the physiological parameter output from the first sensor, obtain, from the physiological parameter, first sequence values of the parameter capable of reflecting the heartbeat of the patient when the first ventilation parameter is used to control the respiratory assistance device to provide respiratory support for the patient, calculate a variation of the first sequence values, evaluate whether the patient is volume responsive based on the variation of the first sequence values, apply an end-expiratory occlusion to the patient when the variation of the first sequence values is less than or equal to a first threshold to respectively obtain values of the parameter capable of reflecting the heartbeat of the patient before and after the end-expiratory occlusion, and determine whether the patient is volume responsive based on a variation of the values of the parameter capable of reflecting the heartbeat of the patient before and after the end-expiratory occlusion.

According to a ninth aspect, a method for evaluating volume responsiveness is provided in an embodiment, the method including:

using a first ventilation parameter to control a respiratory assistance device to provide respiratory support for a patient;

determining whether an evaluation of the volume responsiveness is accurate, and switching the first ventilation parameter to a second ventilation parameter when the evaluation is inaccurate, the second ventilation parameter being capable of increasing a variation of an intrapleural pressure of the patient compared to the first ventilation parameter;

using the second ventilation parameter to control the respiratory assistance device to provide respiratory support for the patient, and collecting a second parameter capable of reflecting a heartbeat of the patient within a predetermined time; and evaluating whether the patient is volume responsive based on a variation of the second parameter.

According to a tenth aspect, a medical device is provided in an embodiment, where the medical device includes:

a respiratory assistance device configured to provide respiratory support for a patient, the respiratory assistance device including a breathing circuit and a ventilation control assembly, wherein the breathing circuit is configured to provide a flow channel for a gas from a gas source to the patient or from the patient to an exhaust port, and the ventilation control assembly is configured to control a flow and/or a pressure of the gas in the breathing circuit;

a first sensor configured to collect a physiological parameter of the patient, where the physiological parameter is at least used to obtain a parameter used to reflect a stroke volume of the patient and capable of reflecting the heartbeat of the patient; and a processor configured to control the ventilation control assembly by using a first ventilation parameter, receive the physiological parameter output from the first sensor, obtain, from the physiological parameter, first sequence values of the parameter capable of reflecting a heartbeat of the patient when the first ventilation parameter is used to control the respiratory assistance device to provide respiratory support for the patient, calculate a variation of the first sequence values, evaluate whether the patient is volume responsive based on the variation of the first sequence values, apply an end-expiratory occlusion to the patient when the variation of the first sequence values is less than or equal to a first threshold to respectively obtain values of the parameter capable of reflecting the heartbeat of the patient before and after the end-expiratory occlusion, and determine whether the patient is volume responsive based on the a variation of the values of the parameter capable of reflecting the heartbeat of the patient before and after the end-expiratory occlusion.

According to an eleventh aspect, a computer-readable storage medium is provided in an embodiment, including a program, the program being executable by a processor to implement the methods described above.

In the foregoing embodiment, when volume responsiveness needs to be evaluated, the intrapleural pressure variation of the patient is increased by changing the ventilation parameters, so that the variation of a parameter that is capable of reflecting the heartbeat of the patient and is used to evaluate the volume responsiveness is also increased, and thus whether the patient is volume responsive when a volume load is increased may be evaluated more accurately.

DETAILED DESCRIPTION

Figure 1:
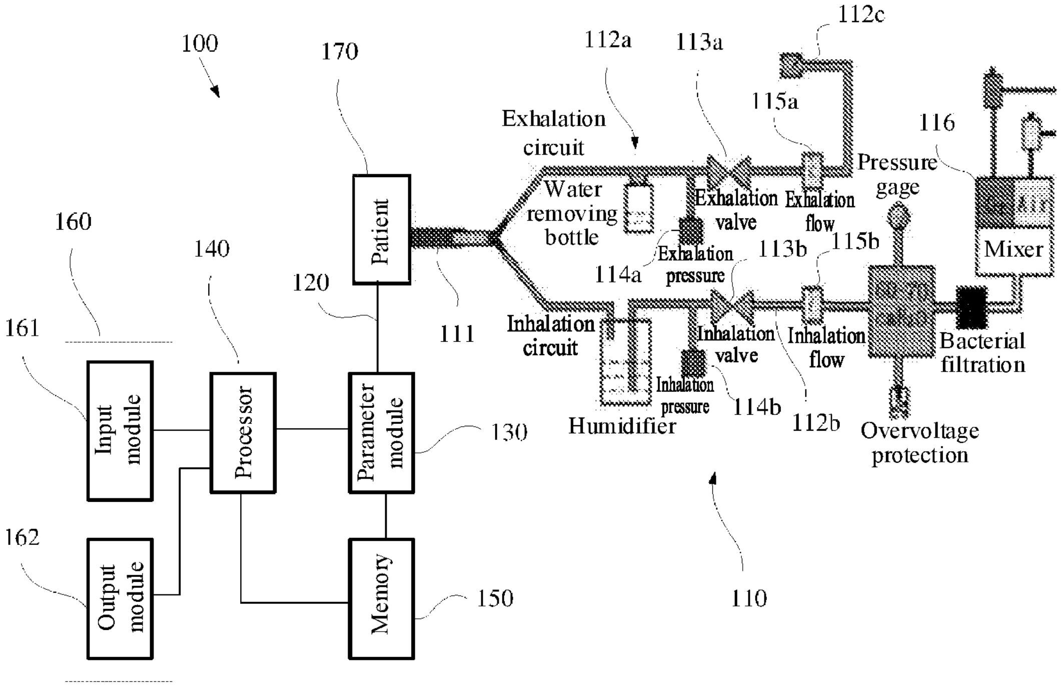
FIG. 1 is a structural schematic diagram of a medical device.

The disclosure will be further described in detail below through specific implementations in conjunction with the accompanying drawings. Associated similar element reference numerals are used for similar elements in different implementations. In the following implementations, many details are described such that the disclosure may be better understood. However, it may be effortlessly appreciated by a person skilled in the art that some of the features may be omitted, or may be substituted by other elements, materials, and methods in different cases. In certain cases, some operations involved in the disclosure are not displayed or described in the specification, which is to prevent a core part of the disclosure from being obscured by too much description. Moreover, for a person skilled in the art, the detailed description of the involved operations is not necessary, and the involved operations can be thoroughly understood according to the description in the specification and general technical knowledge in the art.

In addition, the characteristics, operations, or features described in the specification may be combined in any appropriate manner to form various implementations. Meanwhile, the steps or actions in the method description may also be exchanged or adjusted in order in a way that is obvious to a person skilled in the art. Therefore, the various orders in the specification and the accompanying drawings are merely for the purpose of clear description of a certain embodiment and are not meant to be a necessary order unless it is otherwise stated that a certain order must be followed.

The serial numbers themselves for the components herein, for example, "first" and "second", are merely used to distinguish described objects, and do not have any sequential or technical meaning. Moreover, as used in the disclosure, "connection" or "coupling", unless otherwise stated, includes both direct and indirect connections (couplings).

Referring to FIG. 1, a medical device 100 includes a ventilator 110, a first sensor 120, a parameter module 130, a processor 140, a memory 150, and a human-machine interaction interface 160.

In this embodiment, as a respiratory assistance device, the ventilator 110 is configured to provide respiratory support for a patient. In the embodiment shown in FIG. 1, the ventilator includes a breathing interface 111, a breathing circuit, and a ventilation control assembly. The breathing circuit includes an exhalation circuit 112*a* and an inhalation circuit 112*b*. The exhalation circuit 112*a* is connected between the breathing interface 111 and an exhaust port 112*c*, and is configured to lead out a gas exhaled by a patient 170 to the exhaust port 112*c*. The exhaust port 112*c* may open to external environment, or may open to a dedicated gas recovery apparatus. The inhalation circuit 112*b* is connected between the breathing interface 111 and a gas source 116, and is configured to provide oxygen or air to the patient. The breathing interface 111 is configured to connect the patient to the breathing circuit, so as to introduce a gas output from the gas source 116 to the patient or to introduce the gas exhaled by the patient into the exhaust port 112*c*. According to a situation, the breathing interface 111 may be a nasal cannula or a mask over the nose and mouth. The ventilation control assembly includes an exhalation valve 113*a* and an inhalation valve 113*b*. The exhalation valve 113*a* is disposed in the exhalation circuit 112*a*, and is configured to turn on the exhalation circuit 112*a* or turn off the exhalation circuit 112*a* according to a control instruction, and the inhalation valve 113*b* is disposed in the inhalation circuit 112*b*, and is configured to turn on the inhalation circuit 112*b* or turn off the inhalation circuit 112*b* according to a control instruction. In the embodiment shown in FIG. 1, the ventilator further includes a second sensor for detecting a pressure in the breathing circuit and a third sensor for detecting a flow in the breathing circuit. The second sensor includes an expiratory pressure sensor 114*a* and an inspiratory pressure sensor 114*b*. The expiratory pressure sensor 114*a* is disposed in the exhalation circuit 112*a*, and is configured to sense a gas pressure in a pipeline of the exhalation circuit 112*a*, and convert the detected gas pressure into an electrical signal and output the electrical signal to the processor 140 and/or the memory 150. The inspiratory pressure sensor 114*b* is disposed in the inhalation circuit 112*b*, and is configured to sense a gas pressure in a pipeline of the inhalation circuit 112*b*, and convert the detected gas pressure into an electrical signal and output the electrical signal to the processor 140 and/or the memory 150. The third sensor includes an expiratory flow sensor 115*a* and an inspiratory flow sensor 115*b*. The expiratory flow sensor 115*a* is disposed in the exhalation circuit 112*a*, and is configured to detect a gas flow in the pipeline of the exhalation circuit 112*a*, and convert the detected gas flow into an electrical signal and output the electrical signal to the processor 140 and/or the memory 150. The inspiratory flow sensor 115*b* is disposed in the inhalation circuit 112*b*, and is configured to detect a gas flow in the pipeline of the inhalation circuit 112*b*, and convert the detected gas flow into an electrical signal and output the electrical signal to the processor 140 and/or the memory 150. The gas source 116 is configured to introduce outside air into the inhalation circuit 112*b*, or to mix oxygen and air before the oxygen and the air are introduced into the inhalation circuit 112*b*.

The first sensor 120 is configured to collect a physiological parameter of the patient, and the physiological parameter may include signals such as ECG, EEG, blood pressure, heart rate, blood oxygen, pulse, body temperature. In this embodiment, the collected physiological parameter is at least used to obtain a parameter for reflecting a stroke volume of the patient and capable of reflecting the heartbeat of the patient. The first sensor 120 may be, for example, a pressure sensor for measuring blood pressure. With regard to invasive blood pressure, a catheter is first placed in a blood vessel in a part of the patient to be measured through a puncture, and an outer end of the catheter is directly connected to the first sensor 120 (for example, the pressure sensor). Because a fluid has the effect of pressure transfer, the pressure in the blood vessel will be transferred to the external pressure sensor by liquid in the catheter, so that a dynamic waveform of a real-time pressure change in the blood vessel may be obtained. A systolic pressure, a diastolic pressure and a mean arterial pressure of the blood vessel in the measured part may be obtained by using a specific calculation method in the parameter module 130. The first sensor 120 may alternatively be for example a blood oxygen sensor (not shown) worn on an extremity of the patient, and is configured to collect a blood oxygen signal of the patient for subsequent calculation of blood oxygen saturation. The first sensor 120 may further include an ECG lead and/or an EEG lead for attaching to the patient's body to sense a bioelectric signal of the patient's body.

The parameter module 130 is configured to process the physiological parameter collected by the first sensor 120 to generate a required graphic, image or waveform. The parameter module 130 may be a multi-parameter module, or may include a plurality of separate single-parameter modules.

The memory 150 is configured to store data or a program. For example, the memory 150 may be configured to store a collected physiological parameter or an image frame which is generated by a processor and is not displayed immediately. The image frame may be a 2D or 3D image, or the memory 150 may store a graphical user interface, one or more default image display settings, and a programming instruction for a processor. The memory 150 may be a tangible and non-transitory computer-readable medium such as a flash memory, an RAM, an ROM, and an EEPROM.

The human-machine interaction interface 160 includes an input module 161 and an output module 162. The input module 161 may be, for example, a keyboard, an operation button or a mouse, or may be a touch screen integrated with a display. When the input module is a keyboard or an operation button, a user may directly input operation information or an operation instruction by using the input module. When the input module is a mouse or a touch screen, the user may use the input module together with soft keys, operation icons, menu options and the like on a display interface to complete the input of operation information or operation instructions. The output module 162 is configured to output various monitoring results which may be visually presented to a doctor or other observers in the form of figures, images, text, numbers or charts, or alarm information. In this embodiment, the output module 162 may be a display and/or a printer.

The processor 140 is configured to execute an instruction or a program, process the data output from the parameter module 130, or control the ventilation control assembly. In this embodiment, the processor 140 is configured to control actions of the ventilation control assembly to increase a thoracic pressure of the patient, For example, the processor 140 can increase the thoracic pressure and tidal volume of the patient by means of adjusting ventilation parameters, so as to increase the cardiac output of the patient, then collect a sequence value of a parameter capable of reflecting the heartbeat of the patient within a predetermined time, calculate the variation of the parameter capable of reflecting the heartbeat of the patient, and evaluate whether the patient is volume responsive based on the variation of the parameter capable of reflecting the heartbeat of the patient. In some embodiments, the processor 140 may also evaluate whether the patient is volume responsive based on the variation of the parameter capable of reflecting the heartbeat of the patient before and after the adjustment.

In some embodiments, the parameter module 130 may alternatively be integrated with the processor 140 into a single module.

In some embodiments, the ventilator 10 may alternatively be replaced for other respiratory assistance devices such as an anesthesia machine.

Based on the foregoing medical device, the evaluation process for the volume responsiveness is described below with a pulse pressure variation (PPV) as an example.

Figure 2:
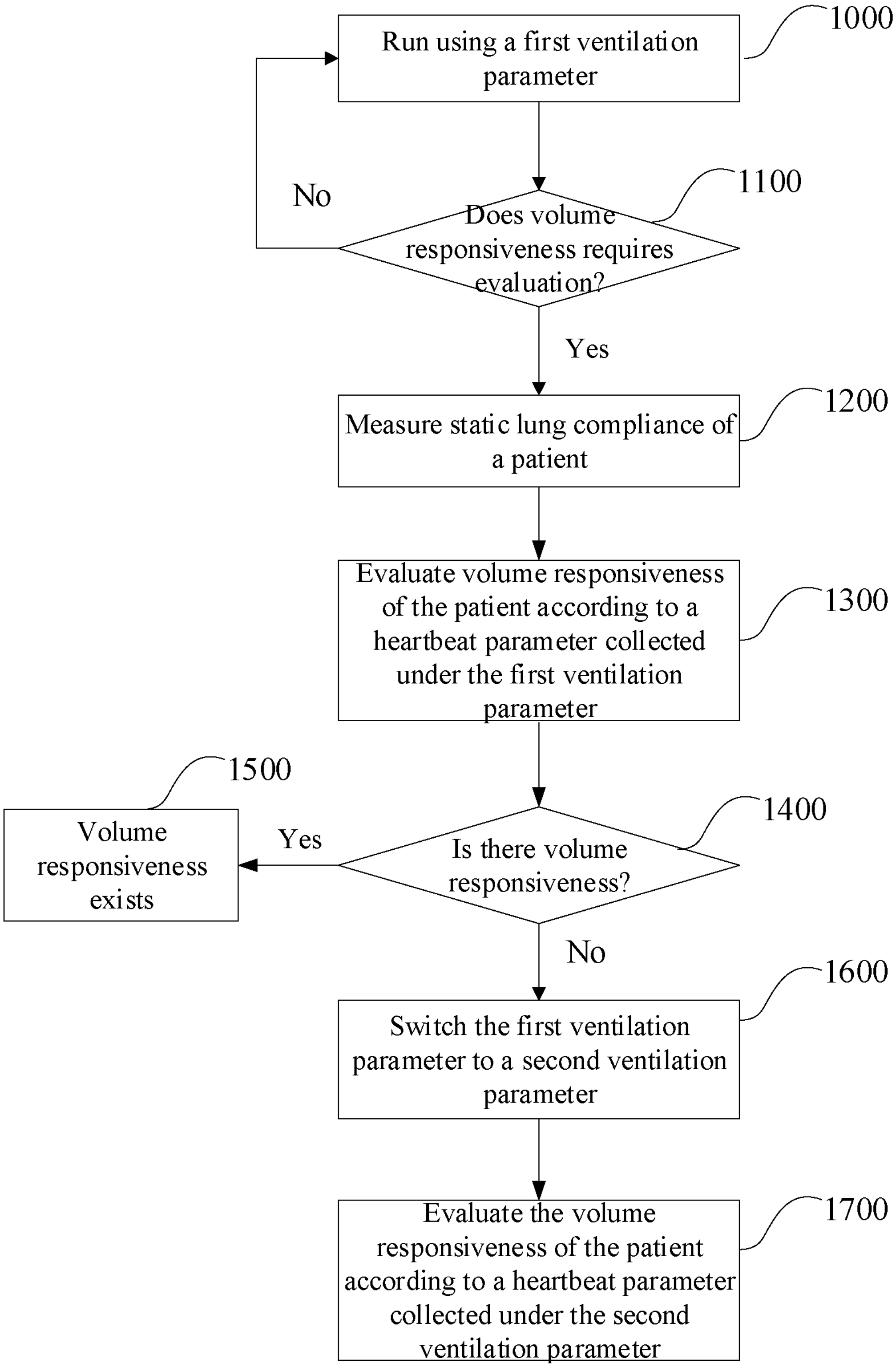
FIG. 2 is a workflow diagram of an embodiment.

In an embodiment, a work flow for evaluating volume responsiveness is shown in FIG. 2, and includes the following steps.

At step 1000, the ventilator 10 may operate using a first ventilation parameter. Under normal circumstances, after an operating mode of the ventilator is selected, the processor 140 uses a preset ventilation parameter to control the actions of the ventilation control assembly, and controls on/off of the breathing circuit and a gas flow and/or a flow rate in each circuit. During the monitoring of the patient, a ventilation parameter may be determined according to specific conditions (such as illness, age and gender) of the patient. The ventilation parameter may be an empirical parameter specifically set by a doctor according to the conditions of the patient or a default parameter set by the ventilator. In a specific embodiment, when the operating mode of the ventilator selected by the user is a volume mode, the ventilation parameter includes a tidal volume. When the operating mode of the ventilator selected by the user is a pressure mode, the ventilation parameter includes an inspiratory pressure. The tidal volume refers to the volume of the gas inhaled or exhaled each time a living organism breathes calmly. Optionally, the tidal volume may be specifically set by the doctor according to the conditions of the patient, or a default tidal volume value of the ventilator may be adopted. When the tidal volume is determined, the processor 140 will control the opening or opening time of the inhalation valve according to the tidal volume, so as to control the gas flow in an airway of the inhalation circuit and change the volume of the gas inhaled by the patient every time. In another embodiment, after the tidal volume is determined, the processor 140 may alternatively control the opening or opening time of the exhalation valve according to the tidal volume, or control the flow rate of the gas delivered by the gas source according to the tidal volume, and control the gas flow in an airway of the exhalation circuit, so as to change the volume of the gas exhaled by the patient every time. Optionally, the ventilation parameter may further include a respiratory rate which may be specifically set by the doctor according to the conditions of the patient or which may take a system default value, and the processor controls a switching frequency of the inhalation valve and the exhalation valve according to the set respiratory rate, thereby controlling the respiratory rate of the patient.

Here, to distinguish from a subsequently modified ventilation parameter, an original ventilation parameter is referred to as a first ventilation parameter and the subsequently modified ventilation parameter is referred to as a second ventilation parameter. Upon that the first ventilation parameter is set, the ventilator uses the first ventilation parameter to provide respiratory support for the patient. In this case, the first sensor 120 collects the physiological parameter of the patient, the second sensor collects the gas pressure data in the breathing circuit, and the third sensor collects the gas flow data in the breathing circuit.

Figure 4:
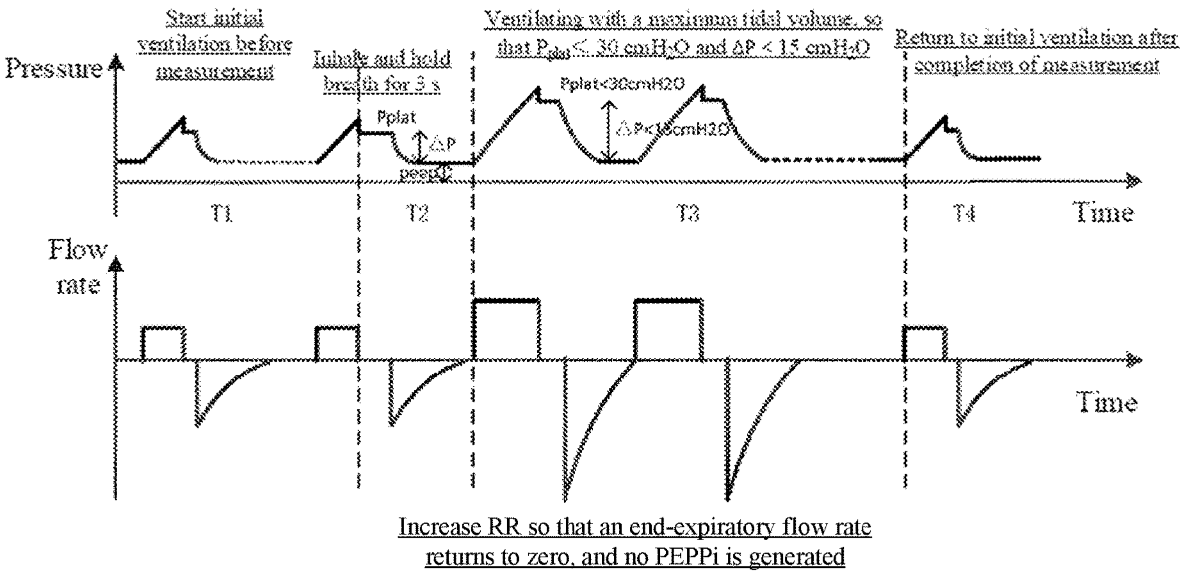
FIG. 4 is a respiratory waveform diagram during operations of a ventilator.

FIG. 4 is a respiratory waveform diagram during the operation of the ventilator. An upper graph shows the changes in the waveform of the gas pressure in the breathing circuit collected by the second sensor as function of time, where a rising phase of the waveform refers to an inspiratory phase and a falling phase of the waveform refers to an expiratory phase. A lower graph shows the changes in the waveform of the gas flow rate in the breathing circuit collected by the third sensor as function of time. The gas flow rate is positive in the inspiratory phase, and is negative in the expiratory phase. After the gas flow rate is obtained, the flow can be calculated from the flow rate and a pipe diameter of the circuit. As shown in FIG. 4, in a stage T1, the ventilator operates by using the first ventilation parameter.

At step 1100, it is determined whether the volume responsiveness needs to be evaluated. The parameter module 130 or the processor 140 receive the physiological parameter output from the first sensor 120, and calculate a hemodynamic parameter of the patient from the physiological parameter. The calculation of the hemodynamic parameter may be performed by using an existing or future algorithm, which will not be described in detail herein. When the hemodynamic parameter is stable, the first ventilation parameter may continue to be used for operation to provide the respiratory support for the patient and the physiological parameter of the patient is monitored at the same time. When the hemodynamic parameter is unstable, step 1200 is performed to start the evaluation of the volume responsiveness.

At step 1200, a compliance of the patient can be measured. The compliance of the patient may refer to the compliance of a respiratory system of the patient or the compliance of the lung of the patient. Taking the compliance of the respiratory system as an example, previous studies have shown that the accuracy of the PPV in predicting the volume responsiveness of the patient with the acute respiratory distress syndrome (ARDS) is significantly reduced when the compliance of the respiratory system (Crs) of the patient is less than 30 ml/cm$H_2O$ is significantly reduced. It is concluded therefrom that excessively low compliance of the respiratory system (Crs) will affect the accuracy of the PPV in evaluating the volume responsiveness. Therefore, in this embodiment, the compliance of the patient is first measured, and when the compliance is less than a certain threshold (for example, Crs<30 ml/cm$H_2O$), a correction coefficient is used to correct the coefficient of a subsequently measured actual PPV.

The compliance of the respiratory system refers to a volume change of the respiratory system of the patient (including the lung and a chest wall) with the change of pressure, where the compliance of the respiratory system includes lung compliance and thoracic compliance. The compliance of the respiratory system can be obtained by measuring an end-inspiratory plateau pressure and a positive end-expiratory pressure (peep), and then dividing the tidal volume by a difference between the end-inspiratory plateau pressure and the positive end-expiratory pressure. For example, if the end-inspiratory plateau pressure is 25, the peep is 5 and the tidal volume is 1000 ml, then Crs is 50.

In a preferred embodiment, the compliance of the respiratory system (Crs) can be tested under the following conditions: the ventilator is controlled to start the end-inspiratory breath hold in a current ventilation mode, as shown in FIG. 4, for a predetermined time (for example, 3 s), which prolongs the duration of a plateau phase $P_{plat}$. During this period, the inspiratory flow rate is monitored. When the gas flow rate drops to 0 (that is, at the time when the gas flow rate enters the plateau phase), a highest airway pressure and the positive end-expiratory pressure (peep) are detected. As shown in FIG. 4, the compliance of the respiratory system (Crs) is detected in a stage T2. The highest airway pressure is the pressure $P_{plat}$ in the plateau phase, and the positive end-expiratory pressure (peep) is the pressure baseline in the breathing circuit, so that the compliance of the respiratory system (Crs) may be calculated.

When measuring the compliance of the respiratory system (Crs) of the patient, whether the patient makes an active inspiratory action may be further monitored, where whether the patient actively inhales during the plateau phase can be detected by monitoring an abnormal change of the waveform of inspiratory flow rate by using a flow sensor arranged in the breathing circuit. When the active inhaling of the patient is detected, measurement result of the compliance of the respiratory system (Crs) is discarded or the current detection is terminated, and re-detection of the Crs is performed.

When the measured compliance of the respiratory system (Crs) is greater than 30 ml/cm$H_2O$, the subsequently measured PPV may not be corrected; when the measured compliance of the respiratory system (Crs) is less than 30 ml/cm$H_2O$, a correction coefficient A is determined based on clinical experiences, and subsequently the measured PPV is corrected by using the correction coefficient A.

In a further embodiment, the step 1200 may be omitted, thereby omitting the correction on the PPV measured subsequently.

At step 1300, the volume responsiveness can be evaluated based on the variation of the parameter capable of reflecting the heartbeat of the patient under the first ventilation parameter. The processor 140 obtains the parameter of the patient capable of reflecting the heartbeat of the patient based on the physiological parameter collected by the first sensor 120, and obtains by calculation a first variation of the parameter capable of reflecting the heartbeat of the patient. The processor 140 samples the physiological parameters collected by the first sensor 120 at sampling intervals, calculates the parameters capable of reflecting the heartbeat of the patient from the sampled values, and may obtain several parameters capable of reflecting the heartbeat of the patient within a preset time period, which are referred to as sequence values of the parameters capable of reflecting the heartbeat of the patient. The variation of the parameter capable of reflecting the heartbeat of the patient is a function of a difference between a maximum value and a minimum value of the sequence values of the parameters capable of reflecting the heartbeat of the patient in a preset time period. The processor 140 then evaluates whether the patient is volume responsive based on the first variation of the parameter capable of reflecting the heartbeat of the patient. The variation of the parameter capable of reflecting the heartbeat of the patient is compared with a preset first threshold. If the variation of the parameter capable of reflecting the heartbeat of the patient is greater than the preset first threshold, the patient is considered to be volume responsive. If the variation of the parameter capable of reflecting the heartbeat of the patient is less than or equal to the preset first threshold, it is considered that the volume responsiveness may not be accurately evaluated, and subsequent steps need to be performed.

The parameter capable of reflecting the heartbeat of the patient is used to reflect a stroke volume of the patient, and the parameter capable of reflecting the heartbeat of the patient may be at least one of a cardiac output, a blood pressure and a pulse oxygen saturation signal. In a specific embodiment, the parameter capable of reflecting the heartbeat of the patient may be the cardiac output, the blood pressure or the pulse oxygen saturation, and a corresponding variation of the parameter capable of reflecting the heartbeat of the patient includes a cardiac output variation, a pulse pressure variation (PPV) or a pulse wave variation. The cardiac output per minute is equal to the stroke volume multiplied by the heart rate. The pulse pressure refers to a difference between the systolic pressure and the diastolic pressure. The pulse oxygen saturation signal refers to a waveform of the blood oxygen saturation as function of the pulse. These parameters may reflect the stroke volume of the patient.

In this embodiment, when the blood pressure is used as the parameter capable of reflecting the heartbeat of the patient, the variation of the parameter capable of reflecting the heartbeat of the patient is the pulse pressure variation (PPV). The pulse pressure variation is denoted as PPVper1 before the ventilation parameter is adjusted, and the pulse pressure variation is denoted as PPVpost after the adjustment.

Figure 3:
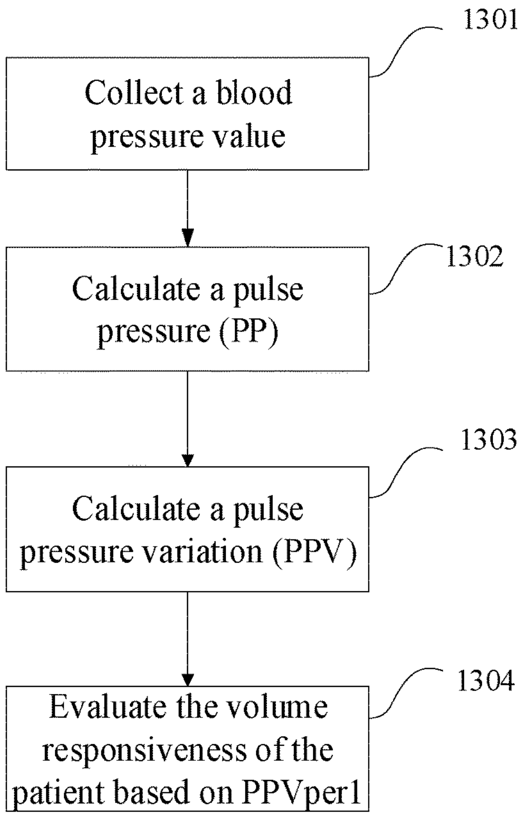
FIG. 3 is a flowchart for evaluating volume responsiveness according to a variation of a first sequence value in an embodiment.

A calculation process and evaluation process for the pulse pressure variation (PPVper1) are shown in FIG. 3, which include the following steps.

At step 1301, blood pressure values are collected. When the first ventilation parameter is used to provide respiratory support for the patient, the systolic pressure and the diastolic pressure of the patient are collected in a predetermined time period to obtain a series of blood pressure values.

At step 1302: a pulse pressure (PP) can be calculated. The pulse pressure (PP) is obtained by calculating the difference between the systolic pressure and the diastolic pressure, so as to obtain a first sequence value of the parameter capable of reflecting the heartbeat of the patient.

Figure 5:
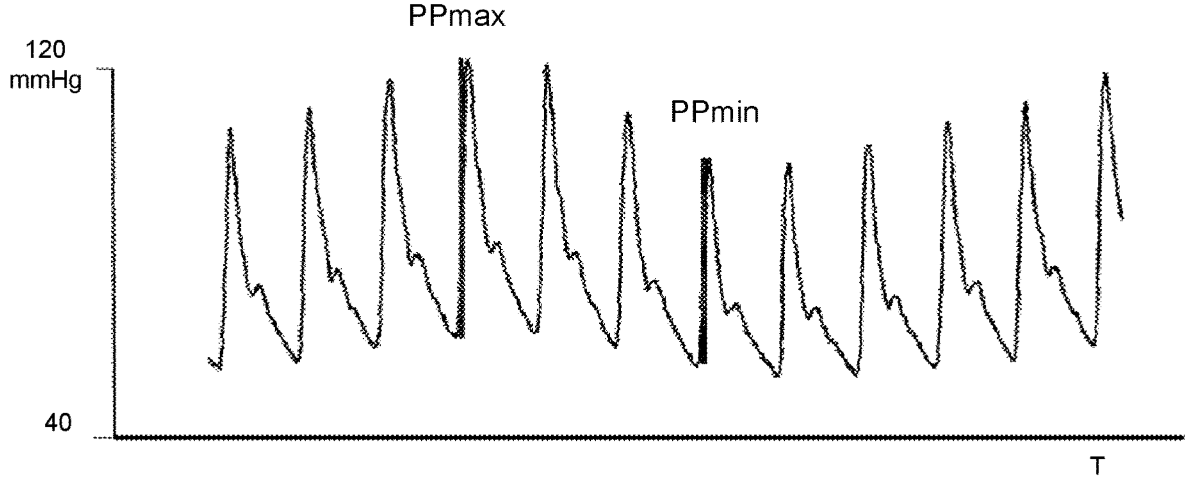
FIG. 5 is a schematic diagram of calculation of a pulse pressure variation (PPV)

At step 1303, a pulse pressure variation (PPV) can be calculated. A maximum value PPmax and a minimum value PPmin of the pulse pressure (PP) within a predetermined time period are looked up. For example, as shown in FIG. 5, the pulse pressure (PP) within a predetermined time period can be formed into a waveform diagram distributed along a time axis, and the pulse pressure variation (PPV) is calculated from the maximum value PPmax and the minimum value PPmin. In this embodiment, a calculation formula for the pulse pressure variation (PPV) is as follows:

$$PPV=2*(PP\,\max-PP\,\min)/(PP\,\max+PP\,\min).$$

The PPV calculated using the above formula under the first ventilation parameter before the adjustment is denoted as the PPVper1.

In other embodiments, the pulse pressure variation (PPV) may alternatively be calculated by using other algorithms, such as PPV=PPmax−PPmin, or PPV=(PPmax−PPmin)/(PPmax+PPmin).

When the compliance of the respiratory system (Crs) measured at the step 1200 is greater than 30 ml/cm$H_2O$, the PPV measured in this step may not be corrected; and when the measured compliance of the respiratory system (Crs) is less than 30 ml/cm$H_2O$, a correction coefficient A is preferably used to correct the PPV measured in this step.

At Step 1304, the volume responsiveness of the patient is evaluated according to the PPVper1. In this embodiment, the PPVper1 is compared with a first threshold R1 to obtain an evaluation result. The first threshold R1 is an empirical value. In this embodiment, the first threshold R1 is set to be equal to 13%. In other embodiments, the first threshold R1 may alternatively be selected as another value.

At step 1400, a step 1500 may be performed when it is determined that PPVper1 is greater than the first threshold R1, and the patient is considered to be volume responsive; otherwise, a step 1600 may be performed.

At step 1600, the first ventilation parameter may be switched to a second ventilation parameter. When the variation of the parameter capable of reflecting the heartbeat of the patient is less than or equal to the preset first threshold, the variation of the parameter capable of reflecting the heartbeat of the patient is relatively small, so that the volume responsiveness may not be evaluated accurately, and thus the variation of the parameter capable of reflecting the heartbeat of the patient needs to be increased. In this embodiment, the intrapleural pressure of the patient is increased by means of adjusting the ventilation parameters. After the intrapleural pressure of the patient in the inspiratory phase increases, the pressure on the heart may be increased, thereby increasing the cardiac output of the patient in this period, which in turn increases the variation of the parameter capable of reflecting the heartbeat of the patient and improves the accuracy of the evaluation of the volume responsiveness by using the variation of the parameter capable of reflecting the heartbeat of the patient. In an embodiment, the intrapleural pressure is increased by means of increasing the tidal volume, for example. This process is referred to as a tidal volume load test. Within the scope of clinical safety, increasing the tidal volume Vt in a short time may make the change of the intrapleural pressure more obvious, and thus improve the accuracy of determining the volume responsiveness of the patient based on the PPV.

When the user selectively operates the ventilator in the volume mode, the change of the intrapleural pressure of the patient may be increased by means of increasing the tidal volume Vt. When the user selectively operates the ventilator in the pressure mode, the change of the intrapleural pressure of the patient may be increased by means of increasing the inspiratory pressure. In essence, the tidal volume increases with the increase in the inspiratory pressure. Therefore, after the ventilation parameter is switched, the second ventilation parameter can increase the tidal volume of the respiratory assistance device compared to the first ventilation parameter.

In this embodiment, the tidal volume of the second ventilation parameter is determined by the maximum allowable values of an airway plateau pressure and a driving pressure. In a preferred embodiment, it is desirable to increase the tidal volume Vt as much as possible within a safe range. For example, the tidal volume is set as the maximum tidal volume of the patient, provided that the safety limit of the mechanical ventilation is met. The maximum tidal volume needs to meet condition that the airway plateau pressure is less than the maximum allowable value of the airway plateau pressure and the driving pressure is less than the maximum allowable value of the driving pressure. The tidal volume used in the second ventilation parameter may be a value less than or equal to the maximum tidal volume. The maximum tidal volume may be specifically determined by the following methods.

In a first method, the maximum tidal volume is determined by automatic setting.

The maximum tidal volume may be determined based on the compliance of the patient, the positive end-expiratory pressure, the maximum allowable value of the airway plateau pressure and the maximum allowable value of the driving pressure. A process for calculating the maximum tidal volume is as follows.

The compliance, the positive end-expiratory pressure, the maximum allowable value of the plateau pressure and the maximum allowable value of the driving pressure are obtained. The compliance and the positive end-expiratory pressure may be obtained by the foregoing calculation. The maximum allowable value of the airway plateau pressure and the maximum allowable value of the driving pressure are preset values respectively, and may be preset by the user (such as a doctor) according to clinical experience, device regulations or guidelines. For example, the compliance C=50 mL/cm$H_2O$, the maximum allowable value of the airway plateau pressure $P_{plat}$ is 30, and the maximum allowable value of the driving pressure $\Delta P$ is 15 cm$H_2O$.

A difference between the maximum allowable value of the airway plateau pressure and the positive end-expiratory pressure is calculated.

The maximum tidal volume is equal to the maximum allowable value of the driving pressure multiplied by the compliance when the difference between the maximum allowable value of the airway plateau pressure and the positive end-expiratory pressure is greater than or equal to the maximum allowable value of the driving pressure. The maximum tidal volume is equal to the difference between the maximum allowable value of the airway plateau pressure and the positive end-expiratory pressure multiplied by the compliance if this difference is less than the maximum allowable value of the driving pressure.

For example, when PEEP is equal to 10 cm$H_2O$, the difference between the maximum allowable value of the airway plateau pressure and the positive end-expiratory pressure is 20, and this difference is greater than the maximum allowable value of the driving pressure of 15 cm$H_2O$, then the maximum tidal volume is equal to the maximum allowable value of the driving pressure multiplied by the compliance. That is, the maximum tidal volume is equal to 15 cm$H_2O$*50 mL/cm$H_2O$=750 mL. When PEEP is equal to 20 cm$H_2O$, the difference between the maximum allowable value of the airway plateau pressure and the positive end-expiratory pressure is 10, and the difference is less than the maximum allowable value of the driving pressure of 15 cm$H_2O$, then the maximum tidal volume is equal to the difference multiplied by the compliance. That is, the maximum tidal volume is equal to 10 cm$H_2O$*50 mL/cm$H_2O$=500 mL.

After the maximum tidal volume is determined, the tidal volume in the second ventilation parameter may be set to be the maximum tidal volume or a certain value less than the maximum tidal volume.

The method for automatically setting the tidal volume requires measurement of the compliance as a premise. According to the description of step 1200, the measurement of the compliance is used to correct the subsequently measured PPV. According to the calculation of the maximum tidal volume, the measurement of the compliance may also be used to calculate the maximum tidal volume. Therefore, when a program has a step of measuring the compliance, a measurement result may be used for at least one of two purposes of correcting the subsequently measured PPV and calculating the maximum tidal volume.

In a second method, the maximum tidal volume is determined by successive approximation. The tidal volume is increased step by step by manual adjustment or automatic adjustment using an algorithm. The processor obtains a tidal volume increasing step by step, detects a real-time airway plateau pressure and a real-time driving pressure under the current tidal volume, respectively compares the real-time airway plateau pressure and the real-time driving pressure with the maximum allowable value of the airway plateau pressure and the maximum allowable value of the driving pressure, and continues to increase the tidal volume when the maximum allowable value of the airway plateau pressure and the maximum allowable value of the driving pressure are not exceeded, so as to gradually approach the maximum tidal volume. When a pressure waveform diagram is displayed on the display interface, the user may also determine the maximum tidal volume according to the real-time pressure waveform diagram.

To prevent the patient from spontaneous breathing in the tidal volume load test, the respiratory rate in the ventilation parameters may also be changed. The respiratory rate in the second ventilation parameter is set to be a maximum safe respiratory rate which does not cause the patient to generate an endogenous end-expiratory pressure in the case of ventilation with the tidal volume or the inspiratory pressure of the second ventilation parameter. The maximum safe respiratory rate which will cause no endogenous PEEP (PEEPi) may be calculated based on the expiratory time under the ventilation using the adopted tidal volume, and is usually 3 times a time constant of a respiratory cycle. The time constant may be calculated by fitting waveform data, or may be calculated by multiplying resistance and compliance. When an inspiratory time and parameters such as PEEP and FiO2 remain unchanged, the maximum respiratory rate does not exceed 30 times/min.

In the absence of PEEPi, increasing the respiratory rate to suppress the spontaneous breathing of the patient as much as possible may further improve the accuracy of the PPV in predicting the volume responsiveness.

The adjusted respiratory rate may alternatively be selected from other values, for example, a value slightly smaller than the maximum safe respiratory rate, as long as the spontaneous breathing of the patient can be suppressed.

When the ventilator monitors that no spontaneous breathing is triggered, or when the set respiratory rate is equal to an actual respiratory rate, it may be considered that the patient does not breathe spontaneously.

In other embodiments, this step may be eliminated if the influences of the spontaneous breathing of the patient are not taken into consideration. Alternatively, this step is replaced with another step. For example, the second sensor and/or the third sensor are/is used to monitor whether the patient breathes spontaneously after switching the ventilation parameters. When there is the spontaneous breathing, the detected PPV may be discarded or the current detection may be terminated, and then the PPV is re-detected.

It should be understood by a person skilled in the art that both the maximum tidal volume and the maximum safe respiratory rate are the best options, but are not necessarily required, and it is not required to meet the two at the same time, as long as the effect of increasing the intrapleural pressure of the patient may be achieved by increasing the tidal volume relative to the current tidal volume, or as long as the effect of increasing the intrapleural pressure of the patient may be achieved by increasing the respiratory rate relative to the current respiratory rate.

In a specific embodiment, the processor switches the ventilation parameter to the second ventilation parameter, for example, by increasing a set value of the tidal volume or the inspiratory pressure in the breathing circuit. Then, the processor uses the second ventilation parameter to control the actions of the ventilation control assembly, so that the gas flow and/or the flow rate in each circuit increase/increases, and the volume of the gas inhaled by the patient every time increases, thereby increasing the variation of the intrapleural pressure of the patient and the cardiac output. When the second ventilation parameter (a larger tidal volume) is used by the ventilator to provide respiratory support for the patient, the first sensor 120 collects the physiological parameter of the patient, the second sensor collects the gas pressure data in the breathing circuit, and the third sensor collects the gas flow data in the breathing circuit.

At step 1700, the volume responsiveness can be evaluated based on the variation of the parameter capable of reflecting the heartbeat of the patient under the second ventilation parameter. The processor 140 obtains the parameter of the patient capable of reflecting the heartbeat of the patient based on the physiological parameter collected by the first sensor 120, obtains a second sequence value of the parameter capable of reflecting the heartbeat of the patient, calculates the variation of the second sequence value, and evaluates whether the patient is volume responsive based on the variation of the second sequence value.

In this step, the pulse pressure variation PPVpost after the ventilation parameter is switched is calculated first. The second ventilation parameter is determined, and the processor controls the actions of the pump valve assembly, so that the ventilator provides respiratory support for the patient by using the second ventilation parameter, operates for a set time by using the second ventilation parameter, such as 5 minutes, and measures the pulse pressure variation PPVpost during the period.

The waveform diagram before and after the ventilation parameter is switched is shown in FIG. 4. When the tidal volume is increased, an inspiratory phase is prolonged, an expiratory phase is shortened, the pressure in the airway is increased, and the airway plateau pressure $P_{plat}$ is correspondingly increased. In this embodiment, the maximum tidal volume with the airway plateau pressure $P_{plat}$ less than 30 $cmH_2O$ and the driving pressure ($\Delta P$) less than 15 $cmH_2O$ is adopted, and the maximum safe respiratory rate which causes on endogenous end-expiratory pressure PEEPi at this maximum tidal volume is used as the respiratory rate. It can be learned from the graph of the flow rate versus time that the flow rate will return to zero before the start of end-expiratory inspiration, and no endogenous end-expiratory pressure PEEPi is generated.

The measurement in this step is performed in a time period T3. For a specific calculation method, reference is made to steps 1301 to 1303. The first sensor collects the physiological parameter of the patient under the second ventilation parameter, and the processor calculates the pulse pressure variation (PPV) from the physiological parameter, denoted as PPVpost.

Like step 1300, when the compliance of the respiratory system (Crs) measured in step 1200 is greater than 30 ml/cm$H_2O$, the PPV measured in this step may not be corrected; and when the measured respiratory compliance (Crs) is less than 30 ml/cm$H_2O$, a correction coefficient A is preferably used to correct the PPV measured in this step.

After the time period T3 elapses, the processor switches the ventilation parameter back to the original first ventilation parameter, so that the ventilator operates by using the first ventilation parameter and enters a time period T4. During the time period T4, the first sensor 120 continuously collects real-time physiological parameters of the patient, the second sensor continuously collects the gas pressure data in the breathing circuit, and the third sensor continuously collects the gas flow rate in the breathing circuit.

After the PPVpost is calculated, the volume responsiveness of the patient is evaluated according to the PPVpost.

During the specific evaluation, whether the patient is volume responsive may only be evaluated based on the variation of the parameter capable of reflecting the heartbeat of the patient after the ventilation parameter is switched, or whether the patient is volume responsive may be evaluated based on the variation of the parameter capable of reflecting the heartbeat of the patient before and after the ventilation parameter is switched. For a specific evaluation method, reference is made to the detailed description below.

Figure 6A:
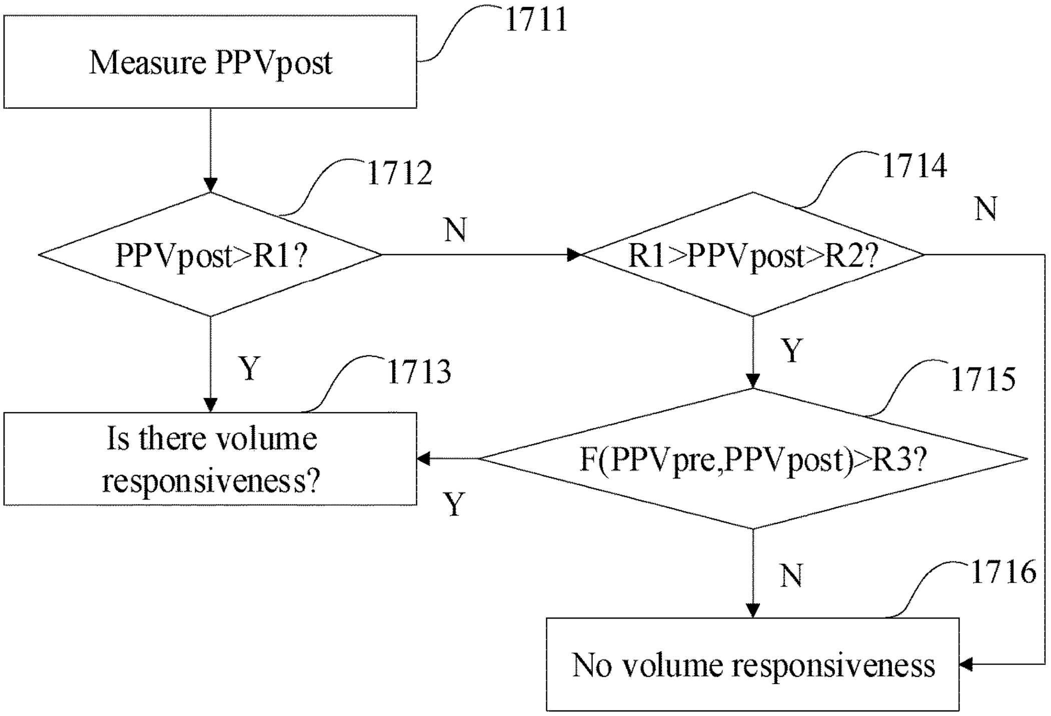
FIGS. 6*a* and 6*b* are respectively flowcharts of two different schemes for evaluating volume responsiveness according to a variation of a second sequence value.

In an embodiment, a flow for evaluating the volume responsiveness according to the PPVpost is shown in FIG. 6*a*, and includes the following steps.

At step 1711, the pulse pressure variation PPVpost is calculated after the ventilation parameter is switched. For the calculation method, reference may be made to the foregoing description. Details are no longer repeated herein.

At Step 1712, it is determined whether the PPVpost is greater than a first threshold R1. When PPVpost is larger than the first threshold, step 1713 will be performed, and the patient is considered to be volume responsive; otherwise, step 1714 will be performed.

At step 1714, it is determined whether the PPVpost is between the first threshold R1 and a second threshold R2. If the PPVpost is between the first threshold and the second threshold, step 1715 will be performed; otherwise, step 1716 will be performed. If the PPVpost is not between the first threshold R1 and the second threshold R2, it means that the PPVpost is less than the second threshold R2. In this case, it is considered that the patient is not volume responsive.

The second threshold R2 is also an empirical value. In this embodiment, the second threshold R2 is set to be equal to 9%. In other embodiments, the second threshold R2 may alternatively be selected as a different value.

At step 1715, the volume responsiveness is evaluated according to the variation of the parameter capable of reflecting the heartbeat of the patient before and after the ventilation parameter switching. If the PPVpost is between the first threshold R1 and the second threshold R2, the volume responsiveness may be evaluated according to a function of the variation of the parameter capable of reflecting the heartbeat of the patient before and after the switching, for example, (PPVpost−PPVper1)/PPVper1.

In another embodiment, after the PPVpost is detected and the ventilation parameter is switched back to the first ventilation parameter or a further third ventilation parameter, the first sensor collects the physiological parameter of the patient under the switched first ventilation parameter or the further third ventilation parameter, and the processor calculates a third sequence value of the parameter of the patient capable of reflecting the heartbeat of the patient within a predetermined time, such as the pulse pressure variation (PPV), denoted as PPVper2. For a specific calculation method, reference is made to steps 1301 to 1303. A function F of the variation of the parameter capable of reflecting the heartbeat of the patient before and after the switching is calculated by using the following formula:

$$F=(\text{PPVpost}-\text{PPVper1})/\text{PPVper2}.$$

If F is greater than a set third threshold R3, it is considered that the patient is volume responsive; otherwise, it is considered that the patient is not volume responsive.

The third threshold R3 is also an empirical value. In this embodiment, the third threshold R3 is set to be equal to 3.5%. In other embodiments, the third threshold R3 may alternatively be selected as a different value.

Figure 6B:
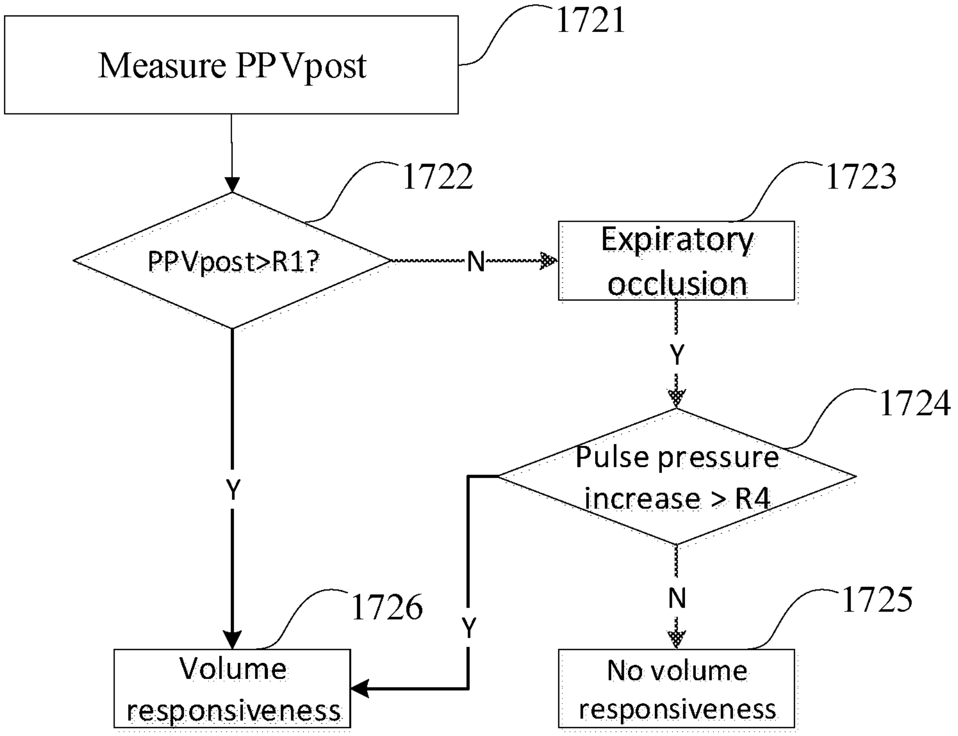

In some embodiments, the end-expiratory occlusion may be further used to assist in determining whether the patient is volume responsive. As shown in FIG. 6*b*, the following steps are included.

At step 1721, the pulse pressure variation PPVpost is calculated after the ventilation parameter is switched. For a calculation method, reference may be made to the foregoing descriptions. Details are no longer repeated herein.

At step 1722, it is determined whether the PPVpost is greater than the first threshold R1. If the PPVpost is greater than the first threshold, step 1726 will be performed, and the patient is considered to be volume responsive; otherwise, step 1723 will be performed.

At step 1723, an expiratory occlusion may be performed.

Figure 7:
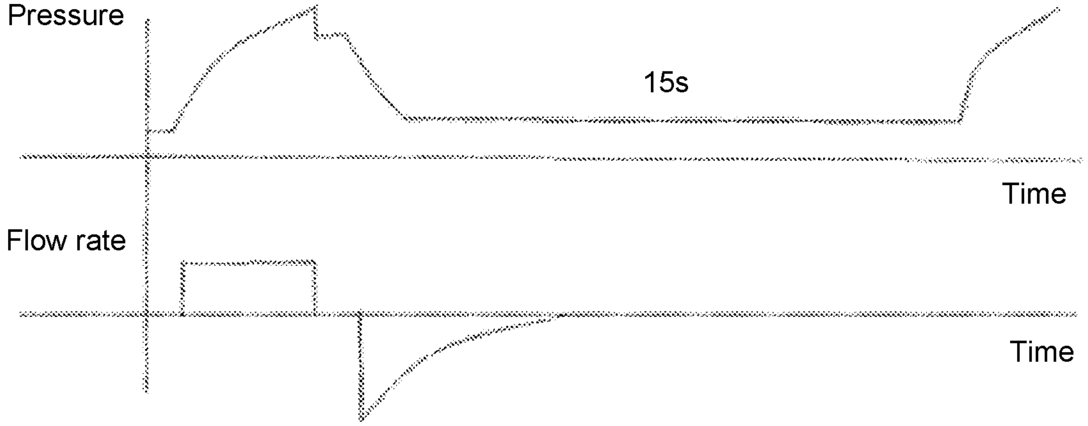
FIG. 7 is a respiratory waveform diagram for expiratory occlusion.

After the PPVpost is detected and the ventilation parameter is switched back to the first ventilation parameter, the exhalation occlusion is performed and maintained for a set time (for example, 15 s), requiring that there is no spontaneous breathing during this time period, and then the pulse pressures (PP) before and after the end-expiratory occlusion are measured. A respiratory waveform diagram of the expiratory occlusion is shown in FIG. 7.

In a preferred embodiment, whether the patient breathes spontaneously is detected within the time of the end-expiratory occlusion. When the spontaneous breathing of the patient is detected, the currently obtained pulse pressure (PP) is discarded or the current detection of the pulse pressure (PP) is terminated, and the pulse pressure (PP) is detected by using the end-expiratory occlusion again.

At step 1724, after the pulse pressures (PP) before and after the end-expiratory occlusion are obtained, it is determined whether the patient is volume responsive based on the change of the pulse pressure (PP). For example, it is determined whether the pulse pressure (PP) after the end-expiratory occlusion is greater than the pulse pressure (PP) before the end-expiratory occlusion by a preset fourth threshold R4. If it is greater than the fourth threshold R4, it is considered that the patient is volume responsive 1726; otherwise, it is considered that the patient is not volume responsive 1725.

The fourth threshold R4 is also an empirical value. In this embodiment, the fourth threshold R4 is set to be equal to 5%. In other embodiments, the fourth threshold R4 may alternatively be selected as a different value.

In addition, the end-expiratory occlusion may also be used in the embodiment shown in FIG. 6*a*. After determining in step 1716 that the patient is not volume responsive, the end-expiratory occlusion may also be applied to the patient to obtain parameters capable of reflecting the heartbeat of the patient before and after the expiratory occlusion, and whether the patient is volume responsive is determined based on the changes of the parameters capable of reflecting the heartbeat of the patient before and after the expiratory occlusion.

In another embodiment, after it is evaluated that the patient is not volume responsive based on the variation of the first sequence values, the end-expiratory occlusion may also be directly applied to the patient to respectively obtain parameters capable of reflecting the heartbeat of the patient before and after the expiratory occlusion, and whether the patient is volume responsive is determined based on the changes of the parameters capable of reflecting the heartbeat of the patient before and after the expiratory occlusion.

In the embodiment shown in FIG. 6*b*, the intrapleural pressure may be reduced by the end-expiratory occlusion, the decrease in the intrapleural pressure leads to an increase in venous return, which in turn gradually increases the blood pumped by the heart, thereby increasing the cardiac output. If the pulse pressure after the end-expiratory occlusion increases relative to the pulse pressure before the end-expiratory occlusion by a relatively large percentage, it means that the end-expiratory occlusion leads to an increase in the cardiac output, and the patient is volume responsive; otherwise, it means that the end-expiratory occlusion cannot increase the cardiac output, and thus the patient is not volume responsive.

In a further improved embodiment, to ensure the safety of the patient, after the ventilation parameter is switched to the second ventilation parameter, the ventilator performs ventilation according to the second ventilation parameter, and when the following conditions are met, the ventilation parameter is switched from the second ventilation parameter to the first ventilation parameter.

In a first condition, after the ventilator performs ventilation for a predetermined time (for example, 5) according to the second ventilation parameter, the processor controls the ventilation parameter to automatically switch from the second ventilation parameter to the first ventilation parameter.

In a second condition, when the ventilator performs ventilation according to the second ventilation parameter, the physiological parameter of the patient is monitored. When the physiological parameter of the patient is abnormal, the processor controls the ventilation parameter to automatically switch from the second ventilation parameter to the first ventilation parameter. For example, when the variation of a heart rate (HR) is greater than 30% of a basic value and the systolic pressure is lower than 80 mmHg, or the variation of a mean arterial pressure (MAP) is greater than 30% of a basic value, and the blood oxygen saturation SPO2 is lower than 85%, the ventilation parameter is automatically switched from the second ventilation parameter to the first ventilation parameter, and the settings of the ventilator are immediately restored to the original settings.

In the foregoing embodiments, when it is determined that the volume responsiveness needs to be evaluated according to the hemodynamic parameter, the variation of the parameter capable of reflecting the heartbeat of the patient measured under a current ventilation parameter is first used to evaluate whether the patient is volume responsive. When the variation of the parameter capable of reflecting the heartbeat of the patient measured under the current ventilation parameter cannot accurately evaluate whether the patient is volume responsive, the ventilation parameter is switched to the second ventilation parameter which can increase the variation of the intrapleural pressure of the patient, and then the variation of the parameter capable of reflecting the heartbeat of the patient measured under the second ventilation parameter is used to evaluate whether the patient is volume responsive. When the second ventilation parameter is used to control the respiratory assistance device to provide respiratory support for the patient, the intrapleural pressure of the patient during inhalation is increased, that is, the pressure on the heart is increased, which increases a difference between the cardiac output of the heart in the inspiratory phase and the cardiac output in the expiratory phase, and the variation of the parameter capable of reflecting the heartbeat of the patient within the set period of time also increases, so that the evaluation accuracy may be improved by the use of the variation of the parameter capable of reflecting the heartbeat of the patient to evaluate the volume responsiveness.

In the foregoing embodiments, when the variation of the first sequence values is less than the preset first threshold and the volume responsiveness may not be accurately evaluated, the ventilation parameter is triggered to switch from the first ventilation parameter to the second ventilation parameter. In further embodiments, other factors may also be used to trigger the ventilation parameter to switch from the first ventilation parameter to the second ventilation parameter. For example, in some embodiments, when the volume responsiveness needs to be evaluated, that is, when it is determined in step 1100 that the volume responsiveness needs to be evaluated, steps 1600 and 1700 may be directly performed to switch the first ventilation parameter currently used for controlling the respiratory assistance device to provide respiratory support for the patient to the second ventilation parameter, collect the second sequence values of the parameter capable of reflecting the heartbeat of the patient within a predetermined time when the second ventilation parameter is used to control the respiratory assistance device to provide respiratory support for the patient, calculate the variation of the second sequence values, and evaluate whether the patient is volume responsive based on the variation of the second sequence values. Directly using the increased variation of the parameter capable of reflecting the heartbeat of the patient to evaluate the volume responsiveness may also achieve the effect of improving the accuracy of the evaluation, but this may bring unnecessary interference to the patient compared to the foregoing embodiments.

Figure 8:
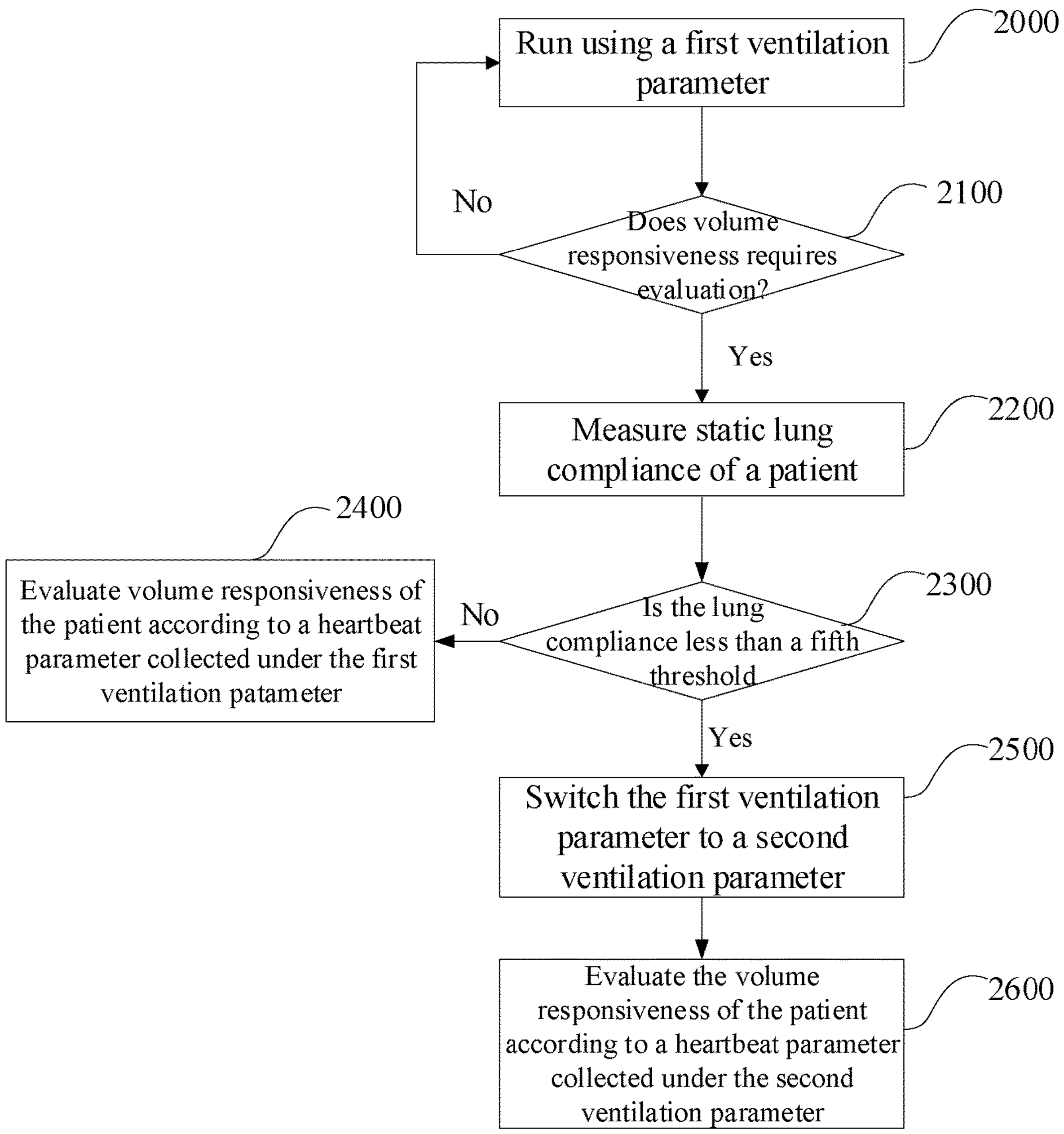
FIG. 8 is a flowchart of evaluating volume responsiveness according to a variation of a second sequence value in another embodiment.

In the embodiment shown in FIG. 8, the ventilation parameter may alternatively be triggered to switch from the first ventilation parameter to the second ventilation parameter by the compliance of the patient. The switching may specifically include the following steps.

At step 2000, the ventilator may run using the first ventilation parameter. This is substantially the same as step 1000.

At step 2100, it is determined whether the volume responsiveness needs to be evaluated. This is substantially the same as step 1100.

At step 2200, the compliance of the patient can be measured. The method for measuring the compliance may be the same as that of step 1200, or, an existing or future method may also be used.

At step 2300, it is determined whether the compliance C is less than a fifth threshold, where the fifth threshold may be an empirical value. For example, it is determined whether the compliance of the respiratory system (Crs) is less than 30 ml/cm$H_2O$, and if Crs is less than 30 ml/cm$H_2O$, step 2500 will be performed; and if Crs is greater than or equal to 30 ml/cm$H_2O$, step 2400 will be performed.

At step 2400, the volume responsiveness is evaluated based on the variation of the parameter capable of reflecting the heartbeat of the patient under the first ventilation parameter. The evaluation method at step 1300 may be used.

At step 2500, the first ventilation parameter is switched to the second ventilation parameter. The second ventilation parameter may be set according to step 1600.

At step 2600, the volume responsiveness can be evaluated based on the variation of the parameter capable of reflecting the heartbeat of the patient under the second ventilation parameter. The evaluation method at step 1700 may be used.

In the foregoing embodiments, whether the patient is volume responsive is evaluated based on the variation of the second sequence value. In some embodiments, it is also possible to assist in evaluating whether the patient is volume responsive based on the end-expiratory occlusion. For example, in the embodiment shown in FIG. 2, step 1723 is performed after it is determined that the PPVper1 is less than or equal to the first threshold R1, and the expiratory occlusion is adopted for determining whether the patient is volume responsive.

Figure 9:
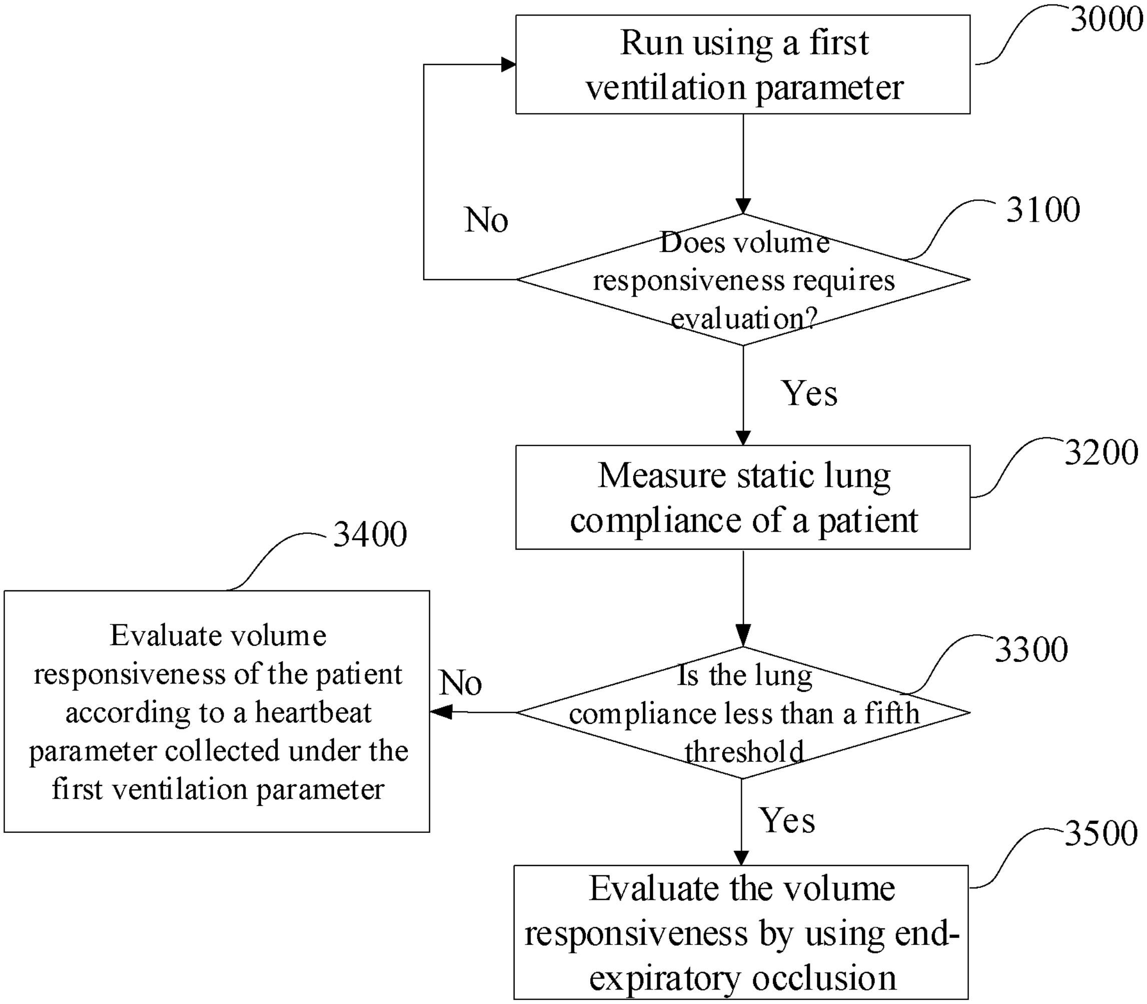
FIG. 9 is a flowchart for evaluating volume responsiveness according to end-expiratory occlusion in an embodiment.

In another embodiment, whether the patient is volume responsive may also be evaluated by means of the end-expiratory occlusion alone as shown in FIG. 9, and the method may include the following steps.

At step 3000, the ventilator may run using the first ventilation parameter. This is substantially the same as step 1000.

At step 3100, it is determined whether the volume responsiveness needs to be evaluated. This is substantially the same as step 1100.

At step 3200, the compliance of the patient may be measured. The method for measuring the compliance may be the same method as that of the step 1200, or, an existing or future method may also be used.

At step 3300, it is determined whether the compliance C is less than the fifth threshold, and the step 3500 is performed if the compliance C is less than the fifth threshold; and the step 3400 is performed if C is greater than or equal to the fifth threshold.

At step 3400, the volume responsiveness is evaluated based on the variation of the parameter capable of reflecting the heartbeat of the patient under the first ventilation parameter. The evaluation method at step 1300 may be used.

At step 3500, the volume responsiveness is evaluated by using the end-expiratory occlusion. The evaluation method from steps 1723 to 1726 may be used.

In some embodiments, the evaluation result of the volume responsiveness may be further displayed on the basis of the foregoing embodiments. For example, the evaluation result of the volume responsiveness may be displayed on a display interface: there is volume responsiveness or there is no volume responsiveness. The clinical accuracy of the evaluation result of the volume responsiveness may be further displayed. For example, when the variation of the parameter capable of reflecting the heartbeat of the patient is greater than a certain threshold, it is considered that there is volume responsiveness; when the variation of the parameter capable of reflecting the heartbeat of the patient substantially exceeds this threshold, it is considered that the evaluation accuracy is relatively high; and when the variation of the parameter capable of reflecting the heartbeat of the patient slightly exceeds this threshold, it is considered that the evaluation accuracy is relatively low. The evaluation result of the volume responsiveness may be represented in percentage, or as a number between 1 and 10, with 1 indicating the minimum accuracy of the evaluation and 10 indicating the maximum accuracy of the evaluation, or the clinical accuracy is represented graphically.

In various embodiments of the disclosure in which the volume responsiveness is evaluated, the patient's body will not be moved. Compared to a solution of improving the accuracy of the evaluation of the volume responsiveness by leg lifting, discomfort of the patient caused by the body moving may be avoided, and the cardiac output may be increased, so that the variation of the parameter capable of reflecting the heartbeat of the patient and used for evaluating the volume responsiveness is increased, thereby improving the accuracy of the evaluation of volume responsiveness.

The description has been made with reference to various example embodiments herein. However, a person skilled in the art should appreciate that changes and modifications may be made to the example embodiments without departing from the scope herein. For example, various operation steps and assemblies for executing operation steps may be implemented in different ways according to a specific application or considering any number of cost functions associated with the operation of the system (for example, one or more steps may be deleted, modified or incorporated into other steps).

In addition, as understood by a person skilled in the art, the principles herein may be reflected in a computer program product on a computer-readable storage medium that is pre-loaded with computer-readable program codes. Any tangible, non-transitory computer-readable storage medium may be used, including magnetic storage devices (hard disks, floppy disks, and the like), optical storage devices (CD-ROM, DVD, Blu Ray disks, and the like), flash memories, and/or the like. These computer program instructions can be loaded onto a general-purpose computer, a dedicated computer, or other programmable data processing apparatus to form a machine, such that these instructions executed on a computer or other programmable data processing apparatus can generate an apparatus that implements a specified function. These computer program instructions may also be stored in a computer-readable memory that may instruct a computer or other programmable data processing apparatus to operate in a specific manner, such that the instructions stored in the computer-readable memory may form a manufactured product, including an implementation apparatus that implements a specified function. The computer program instructions may also be loaded onto a computer or other programmable data processing apparatus, such that a series of operating steps are executed on the computer or other programmable device to produce a computer-implemented process, such that the instructions executed on the computer or other programmable device can provide steps for implementing a specified function.

Although the principles herein have been shown in various embodiments, many modifications of structures, arrangements, ratios, elements, materials, and components that are particularly suitable for specific environments and operating requirements can be made without departing from the principles and scope of the disclosure. The above modifications and other changes or amendments will be included within the scope herein.

The above specific description has been described with reference to various embodiments. However, a person skilled in the art would have appreciated that various modifications and changes could have been made without departing from the scope of the disclosure. Therefore, consideration of the disclosure will be in an illustrative rather than a restrictive sense, and all such modifications will be included within the scope thereof. Likewise, the advantages of various embodiments, other advantages, and the solutions to problems have been described above. However, the benefits, advantages, solutions to problems, and any elements that can produce these, or solutions that make them more explicit, should not be interpreted as critical, necessary, or essential. The term "comprise", "include", and any other variants thereof used herein are non-exclusive, so that the process, method, document, or device that includes a list of elements includes not only these elements, but also other elements that are not explicitly listed or do not belong to the process, method, system, document, or device. Furthermore, the term "coupling" and any other variations thereof used herein refer to physical connection, electrical connection, magnetic connection, optical connection, communication connection, functional connection, and/or any other connection.

A person skilled in the art will recognize that many changes may be made to the details of the above-described embodiments without departing from the basic principles of the disclosure. Therefore, the scope of the disclosure should be determined according to the claims as follows.

What is claimed is:

1. A method for evaluating volume responsiveness, performed by a respiratory assistance device that includes a ventilation control assembly, a processor and a memory storing computer-executable instructions, the method comprising configuring the processor to execute the computer-executable instructions for:

collecting a first sequence of values of a parameter capable of reflecting a heartbeat of a patient within a first predetermined time when a first ventilation parameter is used to control the respiratory assistance device to provide respiratory support for the patient;

calculating a variation of the first sequence of values;

evaluating whether the patient is volume responsive based on the variation of the first sequence of values, and when the variation of the first sequence of values is less than or equal to a first threshold, the method further comprises:

switching the first ventilation parameter to a second ventilation parameter by controlling the ventilation control assembly of the respiratory assistance device to adjust a flow and/or a pressure of a gas in a breathing circuit, wherein the second ventilation parameter is capable of increasing a variation of an intrapleural pressure of the patient compared to the first ventilation parameter;

collecting a second sequence of values of the parameter capable of reflecting the heartbeat of the patient within a second predetermined time when the second ventilation parameter is used to control the respiratory assistance device to provide respiratory support for the patient;

calculating a variation of the second sequence of values;

evaluating whether the patient is volume responsive based on the variation of the second sequence of values;

monitoring, by the processor, a physiological parameter of the patient during the second predetermined time; and automatically switching, by the processor, from the second ventilation parameter back to the first ventilation parameter after the second predetermined time or when the physiological parameter is abnormal.

2. The method of claim 1, wherein the patient is volume responsive when the variation of the first sequence of values is greater than a preset first threshold; or the patient is volume responsive when the variation of the second sequence of values is greater than a preset first threshold.

3. The method of claim 1, wherein the patient is not volume responsive when the variation of the second sequence of values is less than a second threshold, the second threshold being less than the first threshold.

4. The method of claim 1, wherein evaluating whether the patient is volume responsive based on the variation of the second sequence of values comprises:

using a third ventilation parameter to control the respiratory assistance device to provide respiratory support for the patient when the variation of the second sequence of values is between the first threshold and a second threshold, and collecting a third sequence of values of the parameter capable of reflecting the heartbeat of the patient within a third predetermined time; and evaluating whether the patient is volume responsive based on the variation of the first sequence of values, the variation of the second sequence of values, and a variation of the third sequence of values.

5. The method of claim 4, wherein after evaluating whether the patient is volume responsive based on the variation of the first sequence of values, the variation of the second sequence of values, and a variation of the third sequence of values, the method further comprises:

applying an end-expiratory occlusion to the patient to respectively obtain values of the parameter capable of reflecting the heartbeat of the patient before and after the end-expiratory occlusion; and determining whether the patient is volume responsive based on a variation of the values of the parameter capable of reflecting the heartbeat of the patient before and after the end-expiratory occlusion.

6. The method of claim 1, wherein evaluating whether the patient is volume responsive based on the variation of the second sequence of values comprises:

when the variation of the second sequence of values is between the first threshold and a second threshold, applying an end-expiratory occlusion to the patient to respectively obtain values of the parameter capable of reflecting the heartbeat of the patient before and after an end-expiratory occlusion; and determining whether the patient is volume responsive based on the variation of the values of the parameter capable of reflecting the heartbeat of the patient before and after the end-expiratory occlusion.

7. The method of claim 6, further comprising detecting whether the patient breathes spontaneously during the end-expiratory occlusion, discarding a currently obtained value of the parameter capable of reflecting the heartbeat of the patient when the patient is detected to breath spontaneously, and re-using the end-expiratory occlusion to calculate an amplitude increase of the parameter capable of reflecting the heartbeat of the patient.

8. The method of claim 1, wherein before switching the first ventilation parameter to a second ventilation parameter, the method further comprises:

detecting a compliance of the patient;

obtaining a correction coefficient when the detected compliance is less than a fifth threshold; and correcting each of the variation of the first sequence of values and/or the variation of the second sequence of values by the correction coefficient.

* * * * *